(12) United States Patent
Poon

(10) Patent No.: US 11,453,849 B1
(45) Date of Patent: Sep. 27, 2022

(54) MICRO ALGAE CULTURING DEVICE

(71) Applicant: Wing Hei Dennis Poon, Hong Kong (HK)

(72) Inventor: Wing Hei Dennis Poon, Hong Kong (HK)

(*) Notice: Subject to any disclaimer, the term of this patent is extended or adjusted under 35 U.S.C. 154(b) by 0 days.

(21) Appl. No.: 17/517,666

(22) Filed: Nov. 3, 2021

(51) Int. Cl.
*C12M 1/12* (2006.01)
*C09D 133/12* (2006.01)
(Continued)

(52) U.S. Cl.
CPC .......... *C12M 23/06* (2013.01); *A01G 33/00* (2013.01); *C01B 33/12* (2013.01); *C09D 133/12* (2013.01); *C09D 183/04* (2013.01); *C11D 3/1246* (2013.01); *C11D 11/0035* (2013.01); *C12M 23/20* (2013.01); *C12M 23/22* (2013.01); *C12M 23/34* (2013.01); *C12M 29/04* (2013.01); *C12M 31/04* (2013.01); *C12M 31/10* (2013.01); *C12M 33/14* (2013.01); *C12M 37/00* (2013.01); *C12M 41/26* (2013.01); *C12M 41/34* (2013.01); *C12M 41/36* (2013.01); *C12M 41/48* (2013.01); *C12N 1/12* (2013.01); *B82Y 5/00* (2013.01); *B82Y 40/00* (2013.01); *C01P 2004/30* (2013.01);
(Continued)

(58) Field of Classification Search
CPC ...... C12M 23/06; C12M 23/20; C12M 23/22; C12M 23/34; C12M 21/02; C12M 29/04; C12M 31/04; C12M 31/10; C12M 33/14; C12M 37/00; C12M 41/26; C12M 41/34; C12M 41/36; C12M 41/48; C12M 43/06; C12M 1/002; C12N 1/12; C01B 33/12; C09D 133/12; C09D 183/04; C11D 3/1246; C11D 11/0035; C01P 2004/30; C01P 2004/64; C12R 2001/89; B82Y 5/00; B82Y 40/00
USPC ....................................... 435/292.1
See application file for complete search history.

(56) References Cited

U.S. PATENT DOCUMENTS 9,539,525 B2    1/2017  Poon et al.
2014/0004600 A1*  1/2014  Tarassov .............. C12M 21/02
                                              435/292.1
(Continued)

FOREIGN PATENT DOCUMENTS

WO       2013036210 A1     3/2013

OTHER PUBLICATIONS

Azra Newar, Asif Hussain, Naveed Akbar, Abeera Ayaz Ansari, Muneeb Qayyum, Ehsan Ali. "hysical abrasion method using submerged spike balls to remove algal biofilm from photobioreactors." BMC Research Notes, 10, 666, pp. 1-6. 2017 (Year: 2017).*

*Primary Examiner* — Michael L Hobbs

(57) ABSTRACT

Embodiments of the present invention provide an automatic micro algae culturing device and system for self-cleaning, continual automatic algae culturing and irradiant optimizing. The culturing device includes a photosynthesis tubular reactor for micro algae culturing, with transparent cleaning particles to scrape off any unwanted particles or components such as including and not limited to formation of biofilm. The tubular reactor has multiple double-walled glasses. Inner walls of the tubes in the tubular reactor may be coated with superhydrophobic coating to avoid bio film formation, or sticking of any hydro dirt or dust particles. Because the cleaning particles are transparent, they wont block any sunlight for photosynthesis in the tubular reactor.

18 Claims, 4 Drawing Sheets

(51) Int. Cl.
*C12M 1/00* (2006.01)
*C12M 1/26* (2006.01)
*C01B 33/12* (2006.01)
*C12N 1/12* (2006.01)
*A01G 33/00* (2006.01)
*C11D 11/00* (2006.01)
*C11D 3/12* (2006.01)
*C12M 1/34* (2006.01)
*C12M 1/36* (2006.01)
*C09D 183/04* (2006.01)
*B82Y 40/00* (2011.01)
*C12R 1/89* (2006.01)
*B82Y 5/00* (2011.01)

(52) U.S. Cl.
CPC ...... *C01P 2004/64* (2013.01); *C12R 2001/89* (2021.05)

(56) References Cited

U.S. PATENT DOCUMENTS

2015/0329810 A1* 11/2015 Wyatt .................... C12M 23/06
435/292.1
2015/0353865 A1* 12/2015 Poon ......................... B04B 3/00
554/175

\* cited by examiner

MICRO ALGAE CULTURING DEVICE

The present invention is generally related to bio-samples culturing devices. More particularly, the present invention relates to Micro Algae Culturing Device that brings algae culturing up to industrial scale.

BACKGROUND OF INVENTION

Depletion of fossil fuel and green house effect has been disturbing the human race for decades. Scientists keep seeking environmental-friendly regenerative fuels and other new sources of energy to resolve this urgent matter. Algal based fuel is classified as third to fourth class regenerative fuel due to difficulties in culture plant scaling up, high cost in fertilizer and dewatering. Algal fuel scientists often choose open pond to reduce the overhead cost in large scale culturing. Yet the productivity decreased drastically due to cross contamination and increase in biodiversity.

Algae-based biofuels are technically and economically viable and cost competitive, require no additional lands, require minimal water use, and mitigate atmospheric $CO_2$. However, commercial production of microalgae biodiesel is still not feasible due to the low biomass concentration and costly downstream processes.

Thus, there is a need of an efficient closed culturing system capable of continuous culturing, with low energy consumption.

OBJECTIVE OF THE INVENTION

It is an objective of the present invention to provide an efficient closed culturing system.

It is an objective of the present invention to allow for continuous culturing.

It is an objective of the present invention to optimize use of fertilizer which can be the best route to bring algal culturing up to industrial scale.

It is also an objective of the present invention to optimize irradiation while closed culturing.

Another objective of the present invention is to avoid bio film formation while algae culturing.

Yet another objective of the present invention is to prevent cross contamination and increase in biodiversity from initial culturing to harvesting.

To further clarify the advantages and features of the present invention, a more elaborate description of the invention will be rendered by reference to specific embodiments thereof, which is illustrated in the appended drawings. It is appreciated that these drawings depict only typical embodiments of the invention and are therefore not to be considered limiting of its scope.

SUMMARY OF INVENTION

An aspect of the present invention provides an automatic algae culturing system comprising at least one optically transparent photosynthesis tubular reactor for carrying out algae culturing, where walls of the tubular reactor are transparent to avoid blocking of sunlight and coated with a superhydrophobic coating to avoid formation of a biofilm, and wherein the walls of the tubular reactor are made of transparent material, including at least one or both of Bismuth silicate glasses or Polymethyl methacrylate (PMMA), and wherein the superhydrophobic coating is at least of Polydimethylsiloxane (PDMS)/Poly(methyl methacrylate) PMMA solution; cleaning particles coated with cationic silica nano particles (CNP) to scrape off unwanted particles including a biofilm, where the cleaning particles are being run within the tubular reactor with flow of water or liquid into the tubular reactor to scrape off biofilm; a plurality of LED lights installed around the tubular reactor for providing LED light to carry out the algae culturing during night; a plurality of computer controlled solar panels, installed around the tubular reactor, for harvesting the solar energy during day, and providing electrical energy to power the plurality of LED lights during the night; and a dewatering device connected with the tubular reactor for harvesting cultured algae from the tubular reactor and for isolation of biomass from the cultured algae; and wherein, the automatic algae culturing system operates in close system in order to prevent cross contamination and ecosystem diversification from initial culturing in the tubular reactor to harvesting with the dewatering device, and wherein the automatic algae culturing system is self cleaning system due to the CNP coated cleaning particles, and wherein the automatic algae culturing system operates for 24 hours culturing algae using sunlight during day, and using the LED light during night.

An embodiment of the culturing system includes plurality of the tubular reactors that arranged either horizontally one beside the other, or stacked vertically over one another, or in combination.

An embodiment of the culturing system the cleaning particles either have different densities or same densities, wherein the cleaning particles includes at least three types of polymer particles including Liner Low Density Polyethylene (LLDPE) 0.94 g/ml, styrene-butadiene copolymer 1.01 g/ml and Methylmethacrylate-StyreneCopolymer 1.08 g/ml, and wherein size of the polymer particles range between 3 mm-5 mm in diameter, and wherein the cleaning particles clean entire inner surface of the walls of the tubular reactor and also of reservoir that stores algae for culturing.

Another embodiment of the culturing system in the cleaning particles coated with cationic silica nano particles (CNP), a diameter range of the nanoparticle lies from 50-200 nm, and where the cleaning particles coated with cationic silica nano particles (CNP) has cationic acrylate polymer with a length range of 1.8 nm-2.3 nm.

An embodiment of the culturing system further includes one or more heat exchange devices to keep the temperature of the automatic algae culturing system within a range of 15° C. to 30° C. which is the temperature range of keeping the algae for optimal productivity.

Another embodiment of the culturing system includes the tubular reactor is built with double-wall glass with a vacuum in between, and where the vacuum between the double-wall glass of the tubular reactor acts as a thermal insulator, and wherein an outer and an inner diameter of an outside tube in the double-wall glass is 0.08 m and 0.076 m respectively; and wherein an outer and an inner diameter of an inside tube in the double-wall glass is 0.05 m and 0.046 m respectively; and wherein the outside and the inside tubes are built in 8 m long each, 10 loops per culturing system in a horizontal arrangement of the tubular reactors and 7 loops per culturing system in a vertical arrangement of the tubular reactors to minimize overall energy consumption; and wherein the outside and the inside tubes is separated 0.05 m apart due to 180 degrees bend following to the next loop, and wherein circulation of algal culturing is kept at maximum flow speed of 0.6 m/s in the tubular reactors.

Yet another embodiment of the automatic algae culturing system further includes an algae culturing reservoir, and where the algae culturing reservoir is built with a cylindrical tank, and contains 30% of the total volume of the algae culturing system, and wherein the algae culturing reservoir further includes one or more built-in sensors including sensors for monitoring and measuring pH, Turbidity, Dissolved Oxygen, Chemical, water level, and flow rate; a control panel that administrates flow rate of algae into the tubular reactor and administrates flow rate of sterilized water and other sterilized liquid into and out of the tubular reactor; an air blower located at top of the culturing system, and one or more pumps to control the flow rate of algae into the tubular reactor and administrates flow rate of sterilized water and other sterilized liquid into and out of the tubular reactor; a set of mirrors for directing the sunlight towards the tubular reactor for improving photosynthesis, wherein the set of mirrors include at least two semi-transparent mirrors set up at an inclination angle of 45° inclined from ground on East and West sides of the tubular reactor, and at least one regular mirror set up on the ground directly below the tubular reactor, and wherein the reflective surface of the semi-transparent mirrors and the regular mirror is facing inward, towards the tubular reactor, and wherein the combination of the semi-transparent mirrors and the regular mirror gathers more sunlight around the tubular reactor and reflect it off evenly towards the walls of the tubular reactor and the algae inside the tubular reactor gets even light intensities so that photosynthetic efficiency increases.

In an embodiment, the plurality of computer controlled solar panels for harvesting the solar energy, wherein the solar panels include at least two solar panels installed on East and West sides, and at least one solar panel installed on the ground directly below the tubular reactor, and wherein the set of solar panels are controlled by computer-controlled motors to move them from the ground with an inclined angle up to 90° with respect to the ground, and wherein the set of solar panels is facing inward, towards the tubular reactor; and wherein the culturing system also includes other devices including a chemical feeder, a water feeder, and a recycled medium feeder.

An embodiment of the culturing system includes the air blower pumps outside air into the algae culturing reservoir, sparged through plurality of holes present in a front cover of the air blower, the air then goes through a fiber glass filter and a mangosteen filter of the air blower before getting into the culturing system, and the mangosteen filter is used for better filtration of bacteria and other intruder, especially other algae strain An embodiment of the culturing system includes the at least one solar panel installed on the ground directly below the tubular reactor is fixed.

BRIEF DESCRIPTION OF DRAWINGS

For a better understanding of the embodiments of the systems and methods described herein, and to show more clearly how they may be carried into effect, references will now be made, by way of example, to the accompanying drawings, wherein like reference numerals represent like elements/components throughout and wherein:

FIG. 1 illustrates exemplary view of a tubular reactor included in the culturing system, in accordance with an embodiment of the present invention;

FIG. 2 illustrates an exemplary view of the tubular reactor with cleaning particles running inside the tubular reactor included in the culturing system, in accordance with an embodiment of the present invention;

FIG. 3 illustrates the cleaning particles coated with cationic silica nano particles, abbreviated as CNP, in accordance with an embodiment of the present invention;

FIG. 4 illustrates an exemplary view of the cleaning particles coated with cationic silica nano particles removing biofilm from the surface of the tubular reactor, in accordance with an embodiment of the present invention;

FIG. 5 illustrates an exemplary block diagram of the culturing system which can be either vertical or a horizontal tubular system, in accordance with an embodiment of the present invention;

FIG. 6 illustrates an exemplary diagram for an air blower used in the culturing system 100, in accordance with an embodiment of the present invention;

FIG. 7 illustrates an exemplary mirror model of set of mirrors installed in the culturing system, in accordance with an embodiment of the present invention;

FIG. 8 illustrates an exemplary solar panel model of set of solar panels installed in the culturing system, in accordance with an embodiment of the present invention; and FIG. 9 illustrates an exemplary implementation model of the culturing system, in accordance with an embodiment of the present invention.

DETAILED DESCRIPTION OF INVENTION

Figure 1:
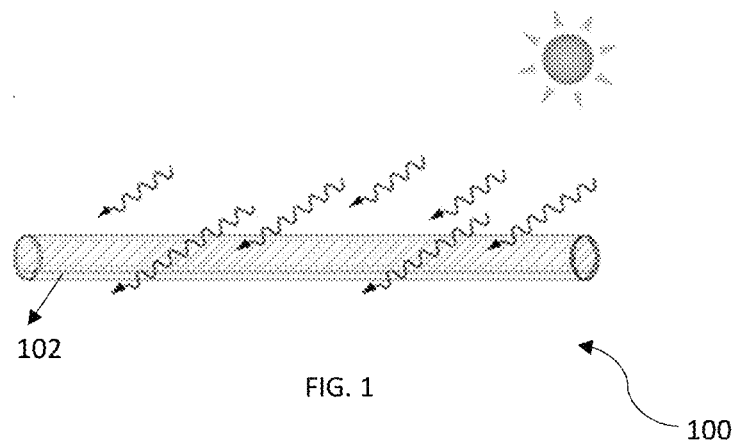
FIGS. 1-9 illustrate different components included in a culturing system, and an exemplary block diagram of the culturing system, in accordance with an embodiment of the present invention.

This patent describes the subject matter for patenting with specificity to meet statutory requirements. However, the description itself is not intended to limit the scope of this patent. The principles described herein may be embodied in many different forms.

Illustrative embodiments of the invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

The present invention provides micro algae culturing device and system for self-cleaning, continual automatic algae culturing and irradiant optimizing. The culturing device includes a photosynthesis tubular reactor for micro algae culturing, with transparent cleaning particles to scrape off any unwanted particles or components such as including and not limited to formation of biofilm. The tubular reactor has multiple double-walled glasses. Inner walls of the tubes in the tubular reactor may be coated with superhydrophobic coating to avoid bio film formation, or sticking of any hydro dirt or dust particles. Because the cleaning particles are transparent, they wont block any sunlight for photosynthesis in the tubular reactor.

In an embodiment, the culturing device includes multiple double-walled bismuth silicate glasses and/or PMMA tubular reactor, cationic coated cleaning particles and other mechanical devices. In order to avoid bio film formation, superhydrophobic coating is applied to the surface of the inner tube. Furthermore, three types of transparent polymer particles with various densities are used to run along with the flow to scrape off any biofilm. Since the cleaning particles are transparent, sunlight will not be blocked inside the tubular reactor during culturing, thus photosynthesis of the culture will not be affected. These cleaning particles with additional cationic nano particles coating are positively charged that keep minimal repulsion from surface (extra cellular polymeric substance matrix) of biofilm. Therefore, they can easily scrape off the biofilm built on the surface of the inner tube surface. Since biofilm is unable to build up in relatively short period of time, hence manual cleaning process is not required as frequent. Therefore, the culture system can keep productivity optimal.

The presenting application operates in a close system in order to prevent cross contamination and increase in biodiversity from initial culturing to harvesting along with centrifugation device for isolation of biomass from algae mixture. Therefore, nutrients in the culture medium can be recycled without getting contamination during operation. In addition, fixed mirrors and solar panels are introduced to increase photosynthetic efficiency and to lower energy cost.

Referring to FIGS. 1-9 that illustrate different components included in the culturing system and device, and an exemplary block diagram of the culturing system, in accordance with an embodiment of the present invention. In FIGS. 1-9, the culturing system is represented by the reference numeral 100.

As mentioned above, the culturing system 100 includes a photosynthesis tubular reactor 102. The tubular reactor 102 provides for an apparatus for carrying out micro algae culturing in it. The walls of the tubular reactor 102 are transparent so the sunlight required for photosynthesis are not blocked, and continuous culturing can be performed.

Sufficient irradiance is essential for algal culturing. The productivity of algae largely depends on the degree of irradiance. Therefore, an optically transparent tubular reactor 102 is needed. The material for manufacturing the walls of the tubular reactor 102 should be highly transparent to allow sunlight through them.

In an embodiment, Bismuth silicate glasses and/or PMMA are chosen because of its high degree of transparency, up to 98.5% highlight transmission (97.5% @ 380 to 720 nm), resistance to salinity, pH fluctuation, weather conditions, corrosion, chemical resistance and uneasy to break. It may be appreciated by the person ordinary skilled in the art that the walls of the tubular reactor 102 can be made of any other suitable transparent material other than Bismuth silicate glasses and/or PMMA, without deviating from the meaning and scope of the present invention.

Biofilm accumulates promptly on the surface of the inner tube during culturing due to surface roughness and hydrophobicity. Excessive amount of biofilm may induce serious diseases to the algal culture, which leads to decrease of productivity ultimately. Therefore, cleaning the inner tubes of a tubular reactor periodically is required to maintain a healthy algal culture. Hence, in the present tubular reactor 102, bismuth silicate glasses and/or PMMA coated with Polydimethylsiloxane (PDMS)/Poly(methyl methacrylate) PMMA solution creates an extremely smooth and hydrophobic surface, which drastically slows down biofilm accumulation, according to an embodiment. It may be appreciated by the person ordinary skilled in the art that the tubular walls of the tubular reactor 102 can be coated with any other suitable material other than Polydimethylsiloxane (PDMS)/Poly(methyl methacrylate)PMMA to create a smooth and hydrophobic surface, without deviating from the meaning and scope of the present invention.

Polydimethylsiloxane (PDMS)/Poly(methyl methacrylate)PMMA coating largely reduces surface roughness, optimizing the rate of photosynthesis and productivity with enhanced light transmission.

Further, the culturing system 100 also includes cleaning particles 104 to scrape off any unwanted particles or components such as including and not limited to formation of biofilm. The cleaning particles 104 are run with the flow within the tubular reactor 102. The culturing system 100 may have different or same types of cleaning particles 104. For example, different or same densities of cleaning particles 104 are used in the culturing system 100. The cleaning particles 104 with densities ranging from lower to higher than but near the density of culture medium can be evenly distributed throughout the system 100 along with the flow. Therefore, the entire of inner surface of the tubular reactor 102 can be cleaned by these cleaning particles 104.

Figure 2:
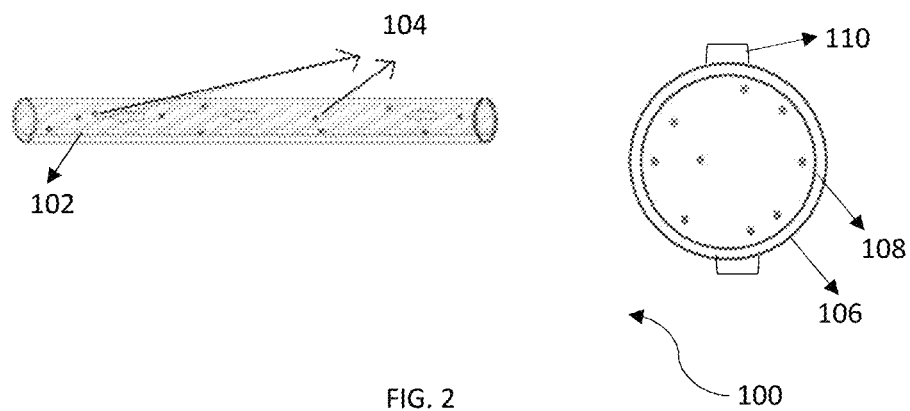
Figure 3:
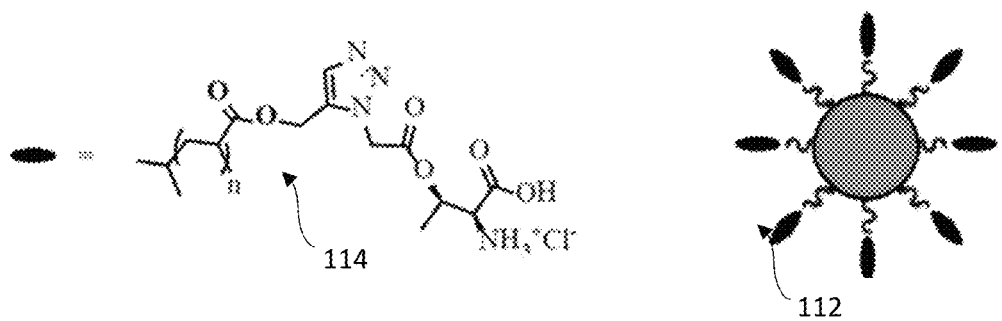
Figure 4:
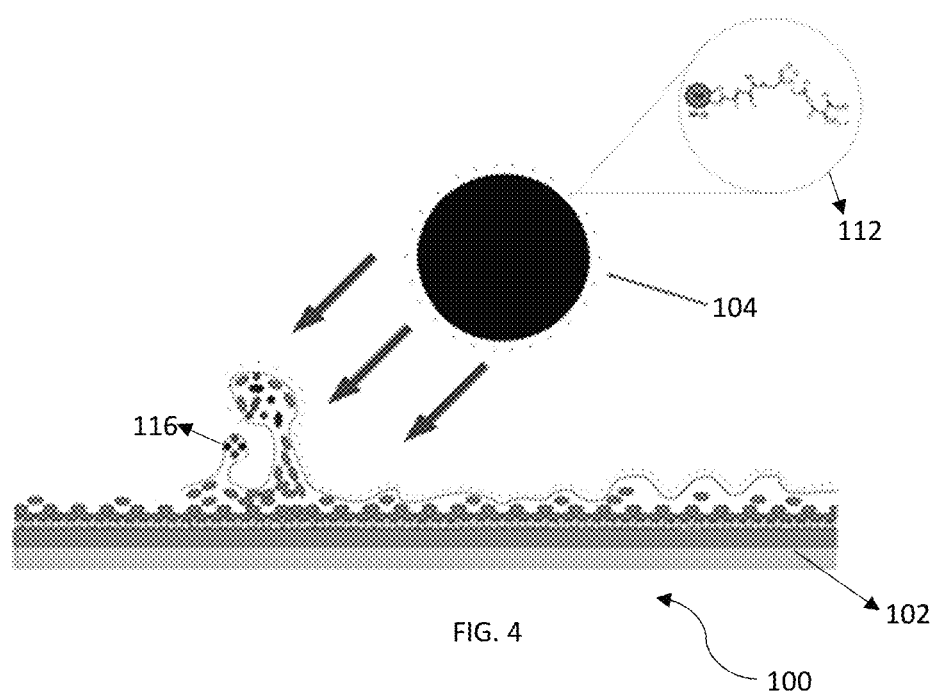

In an embodiment, three types of polymer particles, Liner Low Density Polyethylene (LLDPE) 0.94 g/ml; Styrene-butadiene copolymer 1.01 g/ml and Methylmethacrylate-StyreneCopolymer 1.08 g/ml, size 3-5 mm in diameter, are chosen as cleaning particles 104 to run along with the flow of the culture in the tubular reactor 102 (FIG. 2). These cleaning particles 104 are coated with cationic silica nano particles 112, abbreviated as CNP (FIG. 3). CNP 112 coated cleaning particles 104 exhibit good elasticity and transparency. Since these cleaning particles 104 are positively charged, therefore repulsion force between surface of biofilm formation (116) and the cleaning particles 104 are drastically reduced (FIG. 4). These cleaning particles 104 make random contacts with the surface of the inner tube of the tubular reactor 102, scraping off extracellular polymeric substance before it can start building up as biofilm 116 or any biofilm that is already built up. Therefore, the entire inner surface of the tubular reactor 102 and the reservoir can be cleaned by these CNP 112 coated cleaning particles 104.

In an embodiment, in the cationic silica nano particles 112, the diameter range of the nanoparticle lies from 50-200 nm. In an embodiment, the cationic silica nano particles 112 has cationic acrylate polymer 114 with a length range of 1.8 nm-2.3 nm, and in the molecular representation, "n" is 1. Also, Cationic polymers 114 derivatives on Table 1 are chosen and formulated for CNP production. As shown in the Table 1, cationic acrylate coated nanoparticles exhibit the best elasticity and transparency. However, the other two cationic polymer can also serve for the same purpose. It may be appreciated by the person ordinary skilled in the art that cationic acrylate polymer 114 can be any suitable polymer for providing elasticity and transparency, without deviating from the meaning and scope of the present invention.

TABLE 1
| Cationic polymer | Nature | Structure | Transparency | Elasticity |
| --- | --- | --- | --- | --- |
| Cationic Acrylate | Polysaccharide | 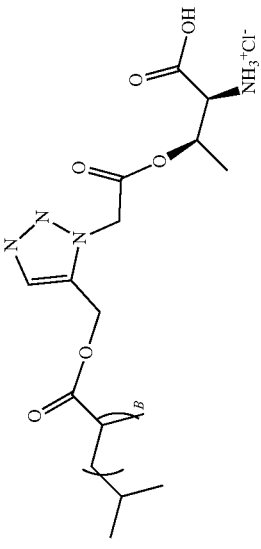 | Opaque | Good |
| Cationic Pyrazole | Polysaccharide | 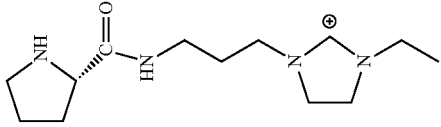 | Opaque | Mild |

TABLE 1-continued
| Cationic polymer | Nature | Structure | Transparency | Elasticity |
|---|---|---|---|---|
| Cationic poly(ester amide) | Cationic arginine and phenylalanine based poly(ester amide)s (Arg-Phe-PEAs) | 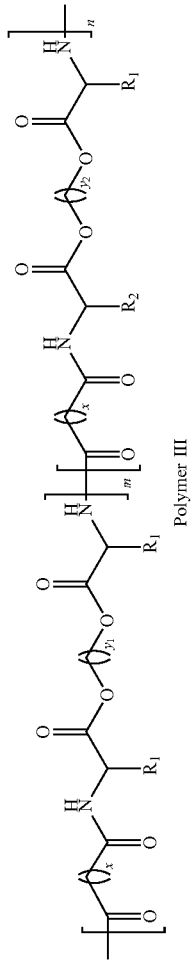<br>Polymer III<br>$R_1 =$ —CH$_2$Ph<br>$R_2 =$ <br>Cationic Arginine and Phenylalanine based poly(ester amide)s/Polymer Positively charged R2 functional group | Opaque | Fair |

In an embodiment, the coating procedure of the cleaning particles 104 includes one or more of the following steps:

Inspection: Check the condition of the target substrate. Make sure transparent polymer particles are in coat-ready condition. 1. Size between 3 to 5 mm in diameter; 2. Surface of the substrate must be well polished; 3. Material and surface has no visible pores or haze.

Cleaning: Clean the substrate surface in deionized water baths with a multi-stage ultra sonic cleaner at 65 degree Celsius for 1 hour. Make sure there is no environmentally damaging additives in substrate holder and stainless steel wire mesh tray.

Pretreatment: After cleaning, the substrate is placed in a degassing vacuum oven to eliminate residues and remove porous with micro blasting.

Surface funtionization: The substrate surface is blasted with oxygen plasma at 30 W 0.2 torr for 60 minutes to ensure surface of substrate are fully oxidized.

Loading: Ensure substrate holders and defining arrangement with reproducible precision. Immerse the substrate in ethanol solution with 0.01 M TESPA for 18 hours. Then substrate will be placed in deionized water bath for 30 minutes ultra-sonication. Substrate will be dried with compressed air before proceeding to the next step.

Coating: Immerse the substrate into 1.0 wt % (CNP) ethanol solution for 10 second. Pull the substrate between 0.50 to 0.75 mm per second. Allow treated substrate dry completely in full nitrogen chamber for 1 hour. Repeat the procedure in 0.8 wt % then in 0.5 wt % (CNP) ethanol solution.

Hydrophobization: The coated substrate is placed in the oven at 90 degree Celsius for 4 hours. Then it is treated with oxygen plasma at 30 W0.3 torr for 60 second. The treated substrate then is transferred to the desiccating chamber filled with perfluorosilane to ensure adhesion between CNP and the substrate are stable.

In an embodiment, the coating procedure of the tubular reactor 102 includes one or more of the following steps:

Inspection: Check quantity, material and surface condition of the target substrate (tubular tubes 102).

Cleaning: Clean the substrate surface in deionized water baths with a multi-stage ultrasonic cleaner.

Pretreatment: The cleaned substrate is placed in a degassing vacuum oven to eliminate residues and remove porous with micro blasting.

Loading: Ensure substrate holders and defining arrangement with reproducible precision. The substrate is coated with 5 to 50 micrometer thick micrometer thick of Polydimethylsiloxane (PDMS)/Poly(methyl methacrylate)PMMA mixture in Tetrahydrofuran (THF) solution. Ratio of the solution is: (1:1:23) Polydimethylsiloxane/Polymethyl methacrylate/Tetrahydrofuran. Then it is heated to 120 degrees Celsius for 60 seconds. The substrate is then placed in aluminum isopropoxide vapor chamber for 10 second.

Next the substrate is transferred to full nitrogen chamber to cool down to room temperature. Then the substrate is coated with a 0.3 micrometer polycrystalline layer of fluorine doped tin oxide.

After the coated substrate is cooled down to room temperature, it is immersed into 0.2 moles/Liter of bismuth neodecanoate and 0.2 moles/Liter di-t-butoxydiacetoxysilane ethanol solutions for 24 hours at room temperature.

Then the substrate is placed in oven at 70 degree Celsius for 3 hours, followed by 600 degree Celsius for 15 minutes.

Finally, the coated substrate is placed in 1% hydrofluoric acid and 99% water ultrasonic bath for 30 minutes after it is cooled down to room temperature.

Allow the treated substrate to dry completely in full nitrogen environment to ensure stability.

The culturing system 100 may include more than one tubular reactors 102 arranged either horizontally one beside the other, or stacked vertically over one another. Furthermore, the algae are best kept between 15° C. and 30° C. for optimal productivity. Therefore, the culturing system 100 may include one or more heat exchange devices (not shown in the figures) installed in the stripper to keep the system 100 temperature within this range. However, heating and cooling the entire system takes a lot of energy. In order to reduce this energy consumption, the tubular reactor 102 is built with double wall glass (106 and 108) with a vacuum in between (FIG. 2).

In an embodiment, the outer and inner diameter of the outside tube (106) is 0.08 m and 0.076 m. In an embodiment, the outer and inner diameter of the inside tube (108) is 0.05 m and 0.046 m. The inside tube 108 with inner diameter under 0.046 m causes higher pressure to circulate the culture, which leads to higher energy consumption. On the other hand, diameter over 0.1 m lowers the biomass concentration, which increases dewatering machine input and thus increases overall operational cost. Therefore, the inner diameter of the inside tube 108 is kept between 0.046 m and 0.1 m. In addition, solar power is harvested to power LED lights 110 during the night in order to retain photosynthetic rate without additional operation cost.

The vacuum between the glass walls (106 and 108) of the tubular reactor 102 acts as a thermal insulator. Therefore, the outside temperature change will have much less effect on the culture medium inside the tubular reactor 102. Thus, much less system heating and cooling is required, resulting much less energy consumption. In an embodiment, the tubes are built in 8 m long each, 10 loops per system in horizontal and 7 loops per system in vertical to minimize overall energy consumption. In an embodiment, both vertical and horizontal systems are built 0.4 meter above ground to avoid dirt formation by either rainfall or flooding. In an embodiment, each tube is separated 0.05 m apart due to 180 degree bend following to the next loop. Circulation of algal culturing is kept at maximum flow speed of 0.6 m/s, in an embodiment.

Figure 5:
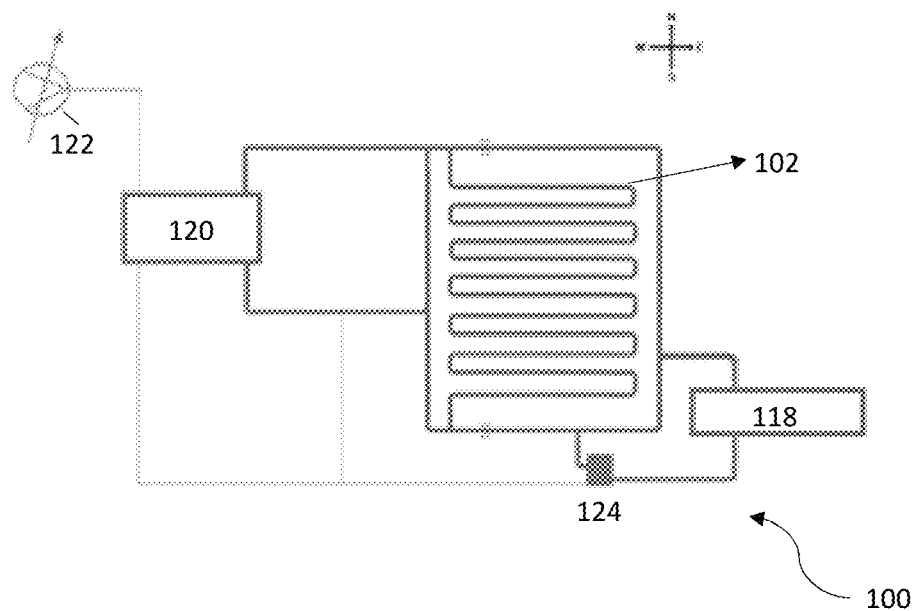

The FIG. 5 is an exemplary block diagram of the culturing system 100 which can be either vertical or a horizontal tubular system. The culturing system 100 as shown in FIG. 5 includes one or more mechanical, electrical, electronic and/or electromechanical components or devices, such as including and not limited to sensors, pump, control panel, a reservoir, an air blower, air filters, water filters, a set of mirrors, a centrifugal device, solar panels, controller for solar panel, and the like.

The culturing system 100 as shown in FIG. 5 includes tubular reactors 102 with running cleaning particles 104 for micro algae culturing. The culturing system 100 operates in strictly close system in order to prevent cross contamination and ecosystem diversification from initial culturing to harvesting along with a centrifugation and dewatering device 118 for isolation of biomass from algae mixture. The centrifugation and dewatering device 118 is the one described in the U.S. Pat. No. 9,539,525B2 owned by Petroleum 2.0 Ltd. Closed system 100 with low energy consumption dewatering device 118 keeps culturing strictly closed from initial culturing to harvesting, which avoids cross contamination and ecosystem diversification.

The culturing system 100 further includes a reservoir and control panel 120 that administrates flow rate and other functions of the culturing system 100. The culturing system 100 further includes an air blower 122 that is located at the top of the system 100. In an embodiment, the air blower 122 is located at a height of 2.2 m to avoid shading issues. The culturing system 100 also includes a pump 124 to control the water flow rate.

In an embodiment, the reservoir 120 is built with a cylindrical tank. It contains 30% of the total volume of the culture system. It has various built-in sensors including and not limited to sensors for pH, Turbidity, Dissolved Oxygen, Chemical, water level, and flow rate. The culturing system 100 may also include other devices such as including and not limited to chemical feeder, water feeder, recycled medium feeder, air blower 122 and an air outlet valve. Each sensor works as following:

A pH sensor keeps track of the pH value. Chemical feeder gradually feeds into the system to retain pH value, for example in the range between 7 and 8.

Turbidity sensor keeps track of the algal culture concentration in the system. It provides the estimate harvesting time.

Dissolved Oxygen sensor keeps track of oxygen level, making sure it never exceeds a prespecified level, such as 300% in the medium. The air blower 122 is turned on with different speeds according to the oxygen level.

Chemical sensor detects the concentration of Nitrogen, Phosphors, Potassium and other essential nutrients. Chemical feeder feeds in various nutrients to keep the concentration at the desired level.

Water level sensor ensures the water level always stays above a prespecified level, such as 50% of the reservoir 120. Harvesting pump 124 is stopped until either water feeder or recycling medium feeder gets the water back to default level.

Circulation pump 124 is controlled by flow rate sensor to keep the flow speed under a prespecified maximum level, for example of 0.6 m/s.

Air outlet valve in the air blower 122 is placed on the top of the tubular system 100 to prevent accumulated air pressure.

Figure 6:
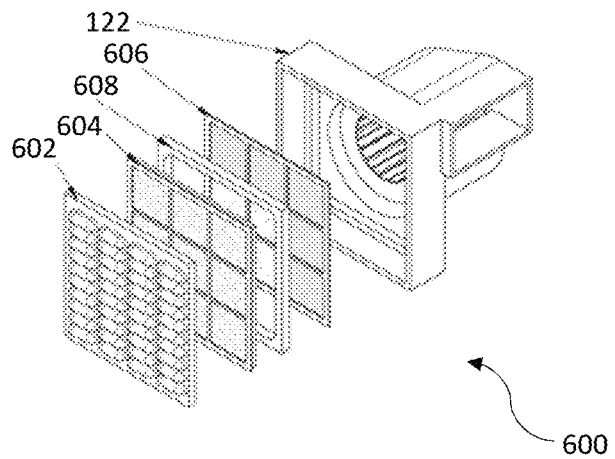

FIG. 6 illustrates an exemplary diagram 600 for the air blower 122 used in the culturing system 100, in accordance with an embodiment of the present invention. The air blower 122 pumps the outside air into the reservoir 120, sparged through numerous holes present in the front cover 602 from the bottom. The holes may be, for example, 1 mm in size. The air goes through a fiber glass filter 604 and a mangosteen filter 606 before getting into the system 100. The fiber glass filter 604 may be for example 30 mm in size and the mangosteen filter 606 is, for example, 20 mm in size.

The Mangosteen filter 606 is used in the culturing system 100 for better filtration of bacteria and other intruder, especially other algae strain. Bacterial filtration efficiency stays up to 97.8% for particles of 3 micron in diameter (mangosteen antibacterial property was patented previously, with patent code WO2013036210 A1). Further, in an embodiment, a spacer 608 can be installed between the fiber glass filter 604 and the mangosteen filter 606 in the air blower 122.

Figure 7:
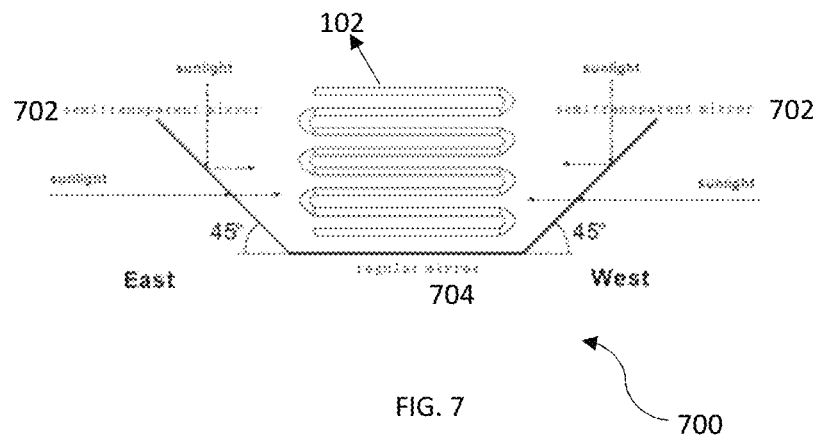

The culturing system 100 may also include a set of mirrors for directing the sunlight towards the tubular reactor 102 for improving photosynthesis. FIG. 7 illustrates an exemplary mirror model 700 of set of mirrors installed in the culturing system 100, in accordance with an embodiment of the present invention. In an embodiment, the tubular reactor 102 are stacked vertically over one another and their walls are facing North-South to reduce shading effect. Semi-transparent mirrors 702 are set up at a suitable inclination angle, for example, an angle of 45° inclined from ground on East and West sides of the tubular reactor 102. Regular mirror 704 is set up on the ground directly below the reactor 102. The reflective surface of the semi-transparent mirrors 702 and the regular mirror 704 is facing inward, towards the tubular reactor 102. The combination of the semi-transparent mirrors 702 and the regular mirror 704 gathers more sunlight around the tubular reactor 102 and reflect it off evenly towards the tubes of the tubular reactor 102. Thus, the algae inside the tubular reactor 102 gets even light intensities so that photosynthetic efficiency increases.

Figure 8:
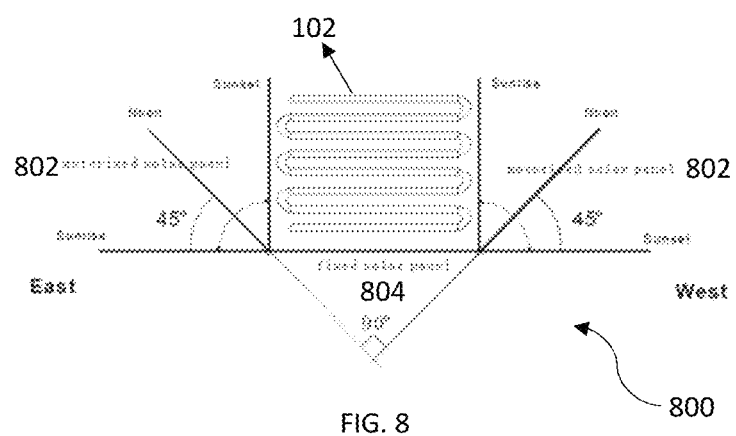

The culturing system 100 also includes computer controlled solar panel for harvesting the solar energy. FIG. 8 illustrates an exemplary solar panel model 800 of set of solar panels installed in the culturing system 100, in accordance with an embodiment of the present invention. In an embodiment, the tubular reactor 102 are stacked vertically over one another and their walls are facing North-South to reduce shading effect. In an embodiment, two solar panels 802 are installed on East and West sides, and one solar panel 804 is installed on the ground directly below the tubular reactor 102. The solar panel 804 below the reactor 102 is fixed. The side solar panels 802 are controlled by motors so that they can rise from the ground with an inclined angle, for example, up to 90° with respect to the ground. These solar panels (802 and 804) are facing inward, towards the reactor 102.

The solar panels 802 and 804 are automatically controlled by a computing controlling panel 120. According to an exemplary situation, the rising angle is set by the controlling panel 120 so that the East side panel (802) lays down flat on the ground during sunrise while the West side panel (802) stands up 90° from the ground. Then gradually the East side panel rises up while the West side panel comes down through the day. At noon, both panels (802 and 804) are inclined 45° from the ground. And at sunset, the East side panel stands up 90° from the ground while the West side panel lays down flat.

The solar panels 802 and 804 turn sunlight into electricity that can power the motors that control the panels. Excess electricity can be stored on batteries to power the LED 110 installed on the reactor tubes 102 (FIG. 2) during night time when sunlight is absent. Combining sunlight during day time and LED 110 light during the night, the algae culture can continue the photosynthesis process up to 18 hours a day (optimal daily photosynthesis time). Advantageously, the solar panels 802 and 804 can also act as partial mirrors reflecting off the sunlight that's not absorbed by the solar panels 802 and 804. The reflected sunlight is evenly distributed onto the reactor 102 tubes so that the algae inside will get even light intensities and therefore photosynthetic efficiency will increase.

Figure 9:
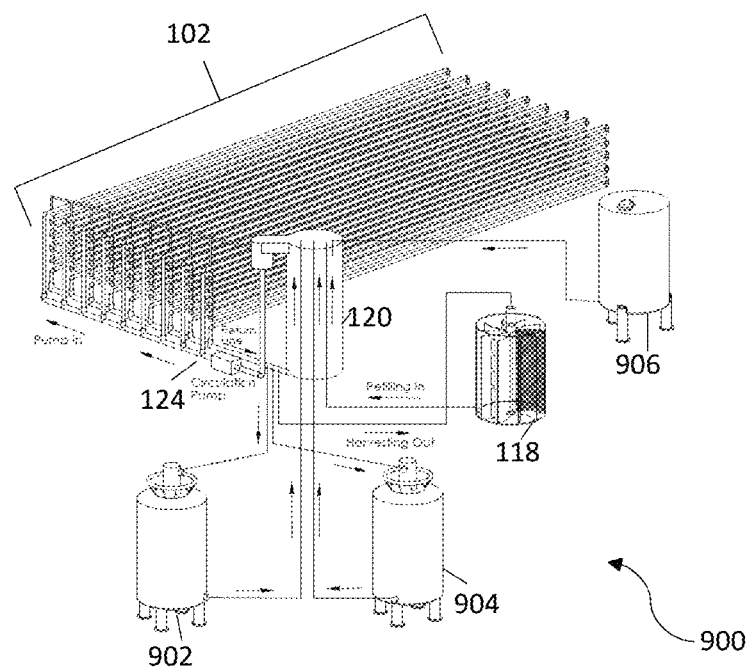

FIG. 9 illustrates an exemplary implementation model 900 of the culturing system 100, in accordance with an embodiment of the present invention. The implementation model 900 of the culturing system 100 includes a plurality of tubular reactors 102. The plurality of the tubular reactors 102 may be arranged horizontally or vertically or in combination. Further in FIG. 9, the culturing system 100 includes a temporary algae culture reserve tank 902 for temporarily reserving the micro algae; a sterilized liquid tank 904 for storing sterilized liquid; a sterilized water tank 906 for storing sterilized water; the dewatering device 118, and the reservoir 120 for the algae.

The Automatic Algal Culturing System 100 is target to be non-stop in operation for 24 hours on the daily basis. In an embodiment, automatic Algal culturing system 100 consists of two individual phases, culturing phase and harvesting phase which are administrated by series of meters and machines connected to a PLC system. The purpose of the PLC system is to monitor the meters readings and control the behavior of the machines by feeding the corresponding protocol signals once the meter readings reach certain conditions. In addition, all relevant meters reading data and the command transaction data are captured for process evaluation, data analysis and troubleshooting purpose.

Sterilized water and liquid can be pumped into and out of the tubular reactors using the sterilized water tank 906 and the sterilized liquid tank 904, respectively via one or more pumps, such as circulation pump 124.

The tubular reactors 102 are fed with the microalgae from the reservoir 120, cultured continuously into the coated tubular reactors 102 using photosynthesis from sunlight in day and LED light in night, with cleaning particles 104 being run into the tubular reactor 102 to avoid formation of biofilm. After being cultured, the micro algae is harvested out and taken into the dewatering and centrifugal device 118 for isolation of biomass from algae mixture. The centrifugation and dewatering device 118 keeps culturing strictly closed from initial culturing to harvesting, which avoids cross contamination and ecosystem diversification.

In both the culturing phase and the harvesting phase, one or more sensor meters are installed for recording one or more measuring units. In an embodiment, the sensor meters and machines (SYS-R1.1 to SYS-R1.11) installed in the culturing phase are shown in the TABLE 2, and the sensor meters and machines installed in the culturing phase administrate and operate individually. Each device/unit will not affect other device/unit unless two or more devices/units were interlinked.

TABLE 2

Phase 1 - Culturing Phase

| Req. ID | Requirement Description |
|---|---|
| SYS-R1.1 | Power meter (1): Energy consumption will be monitor and record |
| SYS-R1.2 | Light measurement (2): Photosynthetically Active Radiation will be monitor and measure throughout the day |
| SYS-R1.3 | Sunshine sensor (3): Sunshine throughout the day will be record and monitor |
| SYS-R1.4 | Gas analysis (4): Air out from the system will be monitor and measure, air flow will be monitor by airflow meter (14) |
| SYS-R1.5 | Temperature (5): Temperature meter monitors overall temperature of the algal culture, water sprinkler system will be activate once it excess 30 degree Celsius |
| SYS-R1.6 | Nutrient meters (6): Level of nitrogen, phosphors and potassium (NPK) will be monitor by nutrient meter (6) and Nutrient Pump (24) will dose nitrate in certain increment once level of nitrogen dropped below designed level. Phosphors oxide will be dose (25) in to the system once level of phosphors dropped below designed level, lastly Potassium nitrate will be dose (27) in to the system once level of potassium dropped below designed level. |
| SYS-R1.7 | Water Flow (7): Water flow meter will give alert when it went over or below designated range |
| SYS-R1.8 | ph Meter (9): pH Level of algal culture will be monitor by pH meter (9) and nutrient reservoir administrated by solenoid valve (15i) will dose 5M Hydrochloric acid solution in certain increment once level of pH gone over 7.5. Nutrient reservoir administrated by solenoid valve (15j) be dose in 5M sodium hydroxide solution in certain increment into the system once level of pH dropped below 6.5. |
| SYS-R1.9 | Dissolved Oxygen (10b): Air blower (16) will be initiate once level of Dissolved Oxygen gone over 300% |
| SYS-R1.10 | Liquid Carbon Dioxide tank (20): Carbon dioxide will be pump in to the system in designed increment control and monitor by MFC (12) |
| SYS-R1.11 | Recirculation meter (14): Recirculation pump (17) will be monitor by recirculation meter (14), meter reading will send out alert when it went over or below designated range |

In an embodiment, the sensor meters and machines (SYS-2.1 to SYS-R2.5) installed in the harvesting phase are shown in the TABLE 3, and the sensor meters and machines installed in the harvesting phase administrate and operate in sequential basis. Each device/unit in the harvesting phase has to be completed accordingly in order to move on to next device/unit until harvesting cycle was completed.

TABLE 3

Phase 2 - Harvesting Phase

| Req. ID | Requirement Description |
|---|---|
| SYS-R2.1 | 1. Turbidity meter (11) reached X level<br>2. Selonoid valve (15a) turn on<br>3. Harvest pump (18a) turn on |
| SYST-R2.2 | 1. Pump (18a) start pumping culture medium into dewatering machine (U.S. Pat. No. 62/008,500) when water meter (8d) reach 95%, Pump (18a) turn off then selonoid valve (15e) turn off then dewatering machine turn on respectively<br>2. Once dewatering finished selonoid valve (15b) turn on then Pump (18b) turn on<br>3. Pump (18b) continue on until water meter (8b) reach zero for 3 minutes then selonoid valve (15b) shut down and selonoid valve (15e) turn on respectively<br>4. Repeat SYS-R2.2 steps 1-3, until water meter (8a) ≤ 50% |
| SYS-R2.3 | 1. When water meter (8a) reach 50% or lower, selonoid valve (15a) will then shut off<br>2. If dewatering machine is on, allow process continue until dewatering process completed (Case of dewatering machine is on then 15a shut off is rare since water level 8a will not change while dewatering machine is activating)<br>3. Pump (18a) start again for 5 minutes then selonoid valve (15e) will turn off<br>4. Dewatering machine start if water meter (8d) ≠ 0<br>5. Dewatering finished then selonoid valve (15e) turn on, Selonoid valve (15b) turn on then Pump (18b) turn on until water meter (8b) reach zero for 5 minutes respectively. Selonoid valve (15b) shut off after Pump (18b) was stopped |
| SYS-R2.4 | 1. When Selonoid valve (15a) (15b), pump (18b) and dewatering machine were off, as well as water meter (8a) ≤ 50%. Solenoid valve (15c) will switch on<br>2. Pump (18c) then turn on until water meter (8c) reach zero for 3 minutes or water meter (8a) reach 100%, Solenoid valve (15c) will be shut off after Pump (18c) was stopped<br>3. Harvesting cycle completed if water meter (8a) reach 100% |
| SYS-R2.5 | 1. Finally, selonoid valve (15d) will be turn on if pump (18c) was stopped and water meter (8a) has not reach 100%,<br>2. Pump (18d) will be turn on until water meter (8a) reach 100%. Solenoid valve (15d) then shut off.<br>3. Harvesting cycle completed |

For the AAC System, the PLC system delivers the functions following the below system requirements as shown in TABLE 4, in an embodiment:

TABLE 4

Phase 1 - Culturing Phase

| Req. ID | Requirement Description |
|---|---|
| PLC-R1.1 | A PCB adaptor is required which for transforming the different comports from the equipment to the common comports; such as serial port, USB port of LAN port, to connect to the PLC unit. |
| PLC-R1.2 | The PLC shall able to connect and receive the data from the comport adaptor. |
| PLC-R1.3 | The PLC shall able to control the equipment via the relevant communication protocol. |
| PLC-1.4 | The PLC shall be able to log the device readings, control events and exception reading in the log file. |
| PLC-1.5 | The log file is constructed in the CSV format which should be able to collect by a MS Windows Server based application server. |
| PLC-1.6 | The application will be a B/S base solution. (The application is not in the current scope). |

Advantageously, coated tubular system 100 with coated tubular reactor 102 with CNP coated cleaning particles 104 prevents biofilm from building up. Self-cleaning system and biofilm free environment allow continuous healthy culturing without any interruption. Also, closed system with low energy consumption dewatering device 118 keeps culturing strictly closed from initial culturing to harvesting, which avoids cross contamination and ecosystem diversification. Culture medium is ensured being recycled without getting contaminated.

Further, the culturing system is operational for 24 hours, during day as well as night, because of the installation of solar panels. During the day, the sunlight promotes the photosynthesis. The solar panel charges the LEDs installed at the tubular reactor, which works during the night to carry out the photosynthesis at night. Hence, the culturing system is operational for 24 hours.

Low productivity of open pond culturing due to increase in biodiversity and cross contamination frustrated many algal scientists in recent years. Open pond system leads industrialization to a dead end. A self-cleaning and continual automatic culturing closed system, as described in the present application, not only by passes time consuming cleaning process, which lowers the overall productivity, most importantly this type of system can be scaled up to size large enough to reduce the operational cost much lower than open system; cross contamination and ecosystem diversification so can be completely avoided. Fertilizer consumption is optimized in recycling base without getting contaminated with in this strictly close culturing system. In addition, solar power is harvested to power LED lights during the night in order to retain photosynthetic rate without additional operation cost.

It is intended that the disclosure and examples be considered exemplary only. Though the present disclosure includes examples from semiconductors chips or assembly, the PCB bridge architecture disclosed herein may be employed for various applications as would be appreciated by one skilled in the art. The references to devices and architectures used here are intended to be applied or extended to the larger scope and should not be construed as restricting the scope and practice of the present invention.

What is claimed is:

1. An automatic algae culturing system comprising:
   at least one optically transparent photosynthesis tubular reactor for carrying out algae culturing, where walls of the tubular reactor are transparent to avoid blocking of sunlight and coated with a superhydrophobic coating to avoid formation of a biofilm, and
   wherein the walls of the tubular reactor are made of transparent material, including at least one or both of bismuth silicate glasses or polymethyl methacrylate (PMMA), and wherein the superhydrophobic coating is at least of polydimethylsiloxane (PDMS)/poly (methyl methacrylate)PMMA solution;
   cleaning particles coated with cationic silica nano particles (CNP) to scrape off unwanted particles including a biofilm, where the cleaning particles are being run within the tubular reactor with flow of water or liquid into the tubular reactor to scrape off biofilm;
   a plurality of LED lights installed around the tubular reactor for providing LED light to carry out the algae culturing during night;
   a plurality of computer controlled solar panels, installed around the tubular reactor, for harvesting the solar energy during day, and providing electrical energy to power the plurality of LED lights during the night; and
   a dewatering device connected with the tubular reactor for harvesting cultured algae from the tubular reactor and for isolation of biomass from the cultured algae; and
   wherein, the automatic algae culturing system operates in close system in order to prevent cross contamination and ecosystem diversification from initial culturing in the tubular reactor to harvesting with the dewatering device, and
   wherein the automatic algae culturing system is self cleaning system due to the CNP coated cleaning particles, and
   wherein the automatic algae culturing system operates for 24 hours culturing algae using sunlight during day, and using the LED light during night.

2. The system of claim 1, wherein the system includes plurality of the tubular reactors that arranged either horizontally one beside the other, or stacked vertically over one another, or in combination.

3. The system of claim 1, wherein the cleaning particles either have different densities or same densities.

4. The system of claim 3, wherein the cleaning particles includes at least three types of polymer particles including liner low density polyethylene (LLDPE) 0.94 g/ml, styrene-butadiene copolymer 1.01 g/ml and methylmethacrylate-styreneCopolymer 1.08 g/ml, and wherein size of the polymer particles range between 3 mm-5 mm in diameter, and wherein the cleaning particles clean entire inner surface of the walls of the tubular reactor and also of reservoir that stores algae for culturing.

5. The system of claim 1, wherein the automatic algae culturing system further includes one or more heat exchange devices to keep the temperature of the automatic algae culturing system within a range of 15° C. to 30° C. which is the temperature range of keeping the algae for optimal productivity.

6. The system of claim 2, wherein the tubular reactor is built with double-wall glass with a vacuum in between, and where the vacuum between the double-wall glass of the tubular reactor acts as a thermal insulator, and
   wherein an outer and an inner diameter of an outside tube in the double-wall glass is 0.08 m and 0.076 m respectively; and wherein an outer and an inner diameter of an inside tube in the double-wall glass is 0.05 m and 0.046 m respectively; and
   wherein the outside and the inside tubes are built in 8 m long each, 10 loops per culturing system in a horizontal arrangement of the tubular reactors and 7 loops per culturing system in a vertical arrangement of the tubular reactors to minimize overall energy consumption; and
   wherein the outside and the inside tubes is separated 0.05 m apart due to 180 degrees bend following to the next loop, and wherein circulation of algal culturing is kept at maximum flow speed of 0.6 m/s in the tubular reactors.

7. The system of claim 1, wherein the automatic algae culturing system further includes
   an algae culturing reservoir, and where the algae culturing reservoir is built with a cylindrical tank, and contains 30% of the total volume of the algae culturing system, and wherein the algae culturing reservoir further includes one or more built-in sensors including sensors for monitoring and measuring pH, turbidity, dissolved oxygen, chemical, water level, and flow rate;

a control panel that administrates flow rate of algae into the tubular reactor and administrates flow rate of sterilized water and other sterilized liquid into and out of the tubular reactor;

an air blower located at top of the culturing system, and one or more pumps to control the flow rate of algae into the tubular reactor and administrates flow rate of sterilized water and other sterilized liquid into and out of the tubular reactor;

a set of mirrors for directing the sunlight towards the tubular reactor for improving photosynthesis, wherein the set of mirrors include at least two semi-transparent mirrors set up at an inclination angle of 45° inclined from ground on East and West sides of the tubular reactor, and at least one regular mirror set up on the ground directly below the tubular reactor, and wherein the reflective surface of the semi-transparent mirrors and the regular mirror is facing inward, towards the tubular reactor, and wherein the combination of the semi-transparent mirrors and the regular mirror gathers more sunlight around the tubular reactor and reflect it off evenly towards the walls of the tubular reactor and the algae inside the tubular reactor gets even light intensities so that photosynthetic efficiency increases; and the plurality of computer controlled solar panels for harvesting the solar energy, wherein the solar panels include at least two solar panels installed on East and West sides, and at least one solar panel installed on the ground directly below the tubular reactor, and wherein the set of solar panels are controlled by computer-controlled motors to move them from the ground with an inclined angle up to 90° with respect to the ground, and wherein the set of solar panels is facing inward, towards the tubular reactor; and wherein the culturing system also includes other devices including a chemical feeder, a water feeder, and a recycled medium feeder.

8. The system of claim 7, wherein the air blower pumps outside air into the algae culturing reservoir, sparged through plurality of holes present in a front cover of the air blower, the air then goes through a fiber glass filter and a mangosteen filter of the air blower before getting into the culturing system, and the mangosteen filter is used for better filtration of bacteria and other intruder, especially other algae strain.

9. The system of claim 7, wherein the at least one solar panel installed on the ground directly below the tubular reactor is fixed.

10. An automatic algae culturing system comprising:

an algae culturing reservoir for providing algae to a tubular reactor;

at least one optically transparent photosynthesis tubular reactor, in connection with the algae culturing reservoir, for carrying out algae culturing, where walls of the tubular reactor are transparent to avoid blocking of sunlight and coated with a superhydrophobic coating to avoid formation of a bio film;

cleaning particles coated with cationic silica nano particles (CNP) to scrape off unwanted particles including a biofilm, where the cleaning particles are being run within the tubular reactor with flow of water or liquid into the tubular reactor to scrape off biofilm;

a plurality of LED lights installed around the tubular reactor for providing LED light to carry out the algae culturing during night;

a plurality of computer controlled solar panels, installed around the tubular reactor, for harvesting the solar energy during day, and providing electrical energy to power the plurality of LED lights during the night;

a set of mirrors, installed around the tubular reactor, for directing the sunlight towards the tubular reactor for improving photosynthesis; and a dewatering device connected with the tubular reactor for harvesting cultured algae from the tubular reactor and for isolation of biomass from the cultured algae; and wherein, the automatic algae culturing system operates in close system in order to prevent cross contamination and ecosystem diversification from initial culturing in the tubular reactor to harvesting with the dewatering device, and wherein the automatic algae culturing system is self cleaning system due to the CNP coated cleaning particles, and wherein the automatic algae culturing system operates for 24 hours culturing algae using sunlight during day, and using the LED light during night.

11. The system of claim 10, wherein the walls of the tubular reactor are either made of bismuth silicate glasses or PMMA or both in combination owing to their high degree of transparency, up to 98.5% highlight transmission, resistance to salinity, pH fluctuation, weather conditions, corrosion, chemical resistance and uneasy to break, and wherein the superhydrophobic coating is at least of polydimethylsiloxane (PDMS)/poly(methyl methacrylate)PMMA solution.

12. The system of claim 11, wherein the system includes plurality of the tubular reactors that arranged either horizontally one beside the other, or stacked vertically over one another, or in combination.

13. The system of claim 10, wherein the cleaning particles either have different densities or same densities.

14. The system of claim 13, wherein the cleaning particles includes at least three types of polymer particles including liner low density polyethylene (LLDPE) 0.94 g/ml, styrene-butadiene copolymer 1.01 g/ml and methylmethacrylate-styreneCopolymer 1.08 g/ml, and wherein size of the polymer particles range between 3 mm-5 mm in diameter, and wherein the cleaning particles clean entire inner surface of the walls of the tubular reactor and also of reservoir that stores algae for culturing.

15. The system of claim 11, wherein the tubular reactor is built with double-wall glass with a vacuum in between, and where the vacuum between the double-wall glass of the tubular reactor acts as a thermal insulator.

16. The system of claim 10, wherein the automatic algae culturing system further includes the algae culturing reservoir, and where the algae culturing reservoir is built with a cylindrical tank, and contains 30% of the total volume of the algae culturing system, and wherein the algae culturing reservoir further includes one or more built-in sensors including sensors for monitoring and measuring pH, turbidity, dissolved oxygen, chemical, water level, and flow rate;

a control panel that administrates flow rate of algae into the tubular reactor and administrates flow rate of sterilized water and other sterilized liquid into and out of the tubular reactor;

an air blower located at top of the culturing system;

one or more pumps to control the flow rate of algae into the tubular reactor and administrates flow rate of sterilized water and other sterilized liquid into and out of the tubular reactor;

the set of mirrors for directing the sunlight towards the tubular reactor for improving photosynthesis, wherein the set of mirrors include at least two semi-transparent mirrors set up at an inclination angle of 45° inclined from ground on East and West sides of the tubular reactor, and at least one regular mirror set up on the ground directly below the tubular reactor, and wherein the reflective surface of the semi-transparent mirrors and the regular mirror is facing inward, towards the tubular reactor, and wherein the combination of the semi-transparent mirrors and the regular mirror gathers more sunlight around the tubular reactor and reflect it off evenly towards the walls of the tubular reactor and the algae inside the tubular reactor gets even light intensities so that photosynthetic efficiency increases;

the plurality of computer controlled solar panels for harvesting the solar energy, wherein the solar panels include at least two solar panels installed on East and West sides, and at least one solar panel installed on the ground directly below the tubular reactor, and wherein the set of solar panels are controlled by computer-controlled motors to move them from the ground with an inclined angle up to 90° with respect to the ground, and wherein the set of solar panels is facing inward, towards the tubular reactor; and one or more heat exchange devices to keep the temperature of the automatic algae culturing system within a range of 15° C. to 30° C. which is the temperature range of keeping the algae for optimal productivity, and wherein the culturing system also includes other devices including a chemical feeder, a water feeder, and a recycled medium feeder.

17. The system of claim 16, wherein the air blower pumps outside air into the algae culturing reservoir, sparged through plurality of holes present in a front cover of the air blower, the air then goes through a fiber glass filter and a mangosteen filter of the air blower before getting into the culturing system, and the mangosteen filter is used for better filtration of bacteria and other intruder, especially other algae strain.

18. The system of claim 16, wherein the at least one solar panel installed on the ground directly below the tubular reactor is fixed.

* * * * *